(12) United States Patent
Jimbo et al.

(10) Patent No.: US 8,721,177 B2
(45) Date of Patent: May 13, 2014

(54) X-RAY CT SCANNER

(75) Inventors: Tomohiko Jimbo, Fujisawa (JP);
Tomonao Takamatsu, Tokyo (JP);
Hideo Kitamura, Tokyo (JP); Rika Hosaka, Yokohama (JP); Hitoshi Hattori, Yokohama (JP); Harunobu Fukushima, Tokyo (JP); Hideo Iwasaki, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 353 days.

(21) Appl. No.: 12/687,320

(22) Filed: Jan. 14, 2010

(65) Prior Publication Data

US 2010/0177863 A1    Jul. 15, 2010

(30) Foreign Application Priority Data

Jan. 14, 2009 (JP) ................. P2009-006122

(51) Int. Cl.
*A61B 6/03* (2006.01)

(52) U.S. Cl.
USPC .......................... 378/199; 378/130

(58) Field of Classification Search
USPC ............... 378/4, 141, 199, 130, 200
See application file for complete search history.

(56) References Cited

U.S. PATENT DOCUMENTS

| | | | | |
|---|---|---|---|---|
| 5,610,968 | A * | 3/1997 | Deucher et al. | 378/200 |
| 6,412,979 | B1 * | 7/2002 | Hell et al. | 378/200 |
| 6,988,827 | B2 * | 1/2006 | Mueller | 378/199 |
| 6,997,609 | B2 * | 2/2006 | McCarthy, Jr. | 378/200 |

FOREIGN PATENT DOCUMENTS

| | | |
|---|---|---|
| JP | 2000-107165 | 4/2000 |
| JP | 2001-093698 | 4/2001 |
| JP | 2001-245878 | 9/2001 |
| JP | 2002-345804 | 12/2002 |
| JP | 2002-367797 | 12/2002 |

OTHER PUBLICATIONS

Japanese Office Action for Japanese Application No. 2009-006122 mailed on Sep. 14, 2012.

* cited by examiner

*Primary Examiner* — Hoon Song
(74) *Attorney, Agent, or Firm* — Amin, Turocy & Watson, LLP

(57) ABSTRACT

According to an aspect of the present invention, there is provided an X-ray CT scanner including: a gantry; a revolving body provided inside the gantry; an X-ray tube assembly provided in the revolving body; a heat radiator provided inside the revolving body so as to be connected to the X-ray tube assembly; a heat storage material provided in the heat radiator and capable of accumulating a heat generated by the X-ray tube assembly; and an X-ray detector provided inside the revolving body so as to oppose the X-ray tube assembly.

9 Claims, 4 Drawing Sheets

FIG. 5

| LATENT HEAT STORAGE MATERIAL | | | MELTING POINT | MELTING HEAT |
|---|---|---|---|---|
| | | | °C | kJ/kg |
| INORGANIC HYDRATED SALT | CALCIUM CHLORIDE HYDRATE | $CaCl_2 \cdot 6H_2O$ | 29.7 | 192 |
| | SODIUM SULFATE HYDRATE | $Na_2SO_4 \cdot 10H_2O$ | 32.4 | 251 |
| | SODIUM THIOSULFATE HYDRATE | $Na_2S_2O_3 \cdot 5H_2O$ | 48 | 197 |
| | SODIUM ACETATE HYDRATE | $CH_3COONa \cdot 3H_2O$ | 58 | 264 |
| ORGANIC COMPOUND | PARAFFIN | $C_{18}H_{38}$ | 28.2 | 243 |
| | | $C_{20}H_{42}$ | 36.4 | 247 |
| | | $C_{22}H_{46}$ | 44 | 157 |

X-RAY CT SCANNER

CROSS-REFERENCE TO RELATED APPLICATIONS

This application claims priority from Japanese Patent Application No. 2009-006122 filed on Jan. 14, 2009, the entire contents of which are incorporated herein by reference.

BACKGROUND OF THE INVENTION

1. Field of the Invention

An aspect of the present invention relates to an X-ray CT scanner and, in particular, to an X-ray CT scanner provided with the cooling mechanism therefor.

2. Description of the Related Art

In an X-ray computed tomography scanner (X-ray CT scanner), when heat generated by an X-ray tube and the like is accumulated inside a gantry, a failure may be caused. Thus, a mechanism for efficiently discharging the heat is required.

JP-2001-245878-A discloses a technique for the X-ray CT scanner in which a heat storage material is arranged inside an air inlet tube provided in a gantry so that inlet air is cooled by the heat storage material.

However, in the above X-ray CT scanner, since the heat storage material is arranged inside the air inlet tube of the gantry, the inside of the gantry is not efficiently cooled.

SUMMARY OF THE INVENTION

According to an aspect of the present invention, there is provided an X-ray CT scanner including: a gantry; a revolving body provided inside the gantry; an X-ray tube assembly provided in the revolving body; a heat radiator provided inside the revolving body so as to be connected to the X-ray tube assembly; a heat storage material provided in the heat radiator and capable of accumulating a heat generated by the X-ray tube assembly; and an X-ray detector provided inside the revolving body so as to oppose the X-ray tube assembly.

According to another aspect of the present invention, there is provided an X-ray CT scanner including: a gantry; a revolving body provided inside the gantry; an X-ray tube assembly provided in the revolving body; a heat radiator provided inside the revolving body so as to be connected to the X-ray tube assembly; a heat storage material provided in the heat radiator and capable of accumulating a heat generated by the X-ray tube assembly when the X-ray tube assembly emits an X-ray while the revolving body revolves; an X-ray detector provided inside the revolving body so as to oppose the X-ray tube assembly; and a cooling unit provided outside the revolving body so as to oppose the heat radiator in a non-operated state, the cooling unit including at least one of a fan and a radiator.

BRIEF DESCRIPTION OF THE DRAWINGS

FIG. 5 lists heat storage materials.

DETAILED DESCRIPTION OF THE INVENTION

Figure 1:
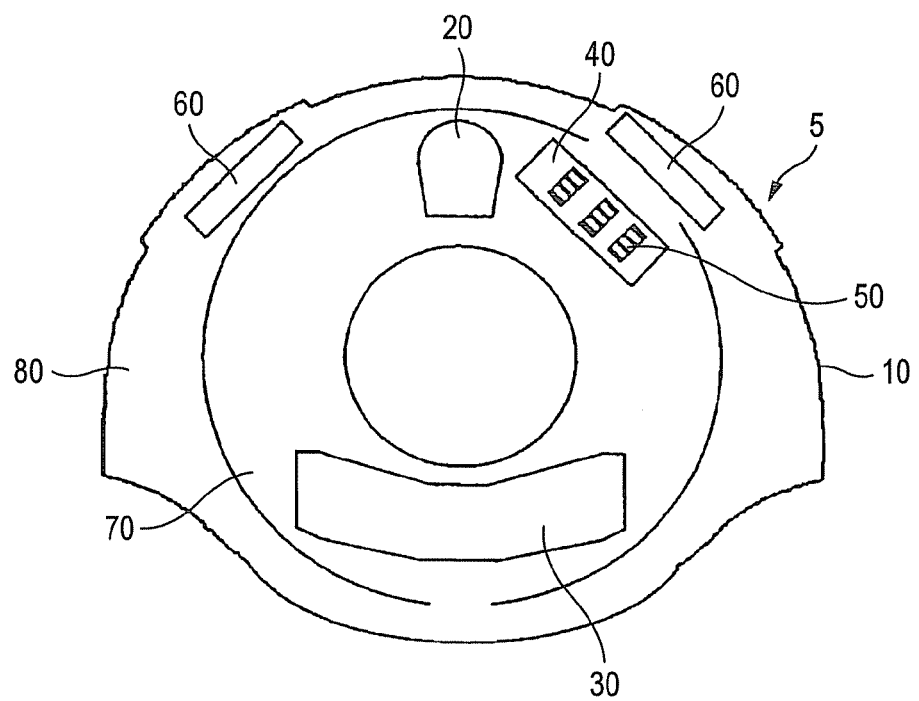
FIG. 1 illustrates a gantry of an X-ray CT scanner according to the embodiment.

An embodiment of the present invention is described below with reference to the drawings.

In the drawings described below, like numerals indicate like parts, and hence their description is omitted.

FIG. 1 illustrates an X-ray CT scanner according to an embodiment.

The X-ray CT scanner of the present embodiment has a revolving body 70 inside a gantry 5. An X-ray tube assembly 20 is provided inside the revolving body 70.

The X-ray tube assembly 20 is connected to a heat radiator 40 provided inside the revolving body 70. In the heat radiator 40, a heat storage material 50 is provided for absorbing heat generated by the X-ray tube assembly 20.

An X-ray detector 30 is provided inside the revolving body 70 to oppose the X-ray tube assembly 20. The X-ray detector 30 detects X-ray projected by the X-ray tube assembly 20.

Further, the gantry 5 includes a gantry cover 10 as an outer cover.

The X-ray tube assembly 20 is used for projecting X-ray onto a test body (not shown), and is arranged and attached to the revolving body 70.

The X-ray detector 30 is installed in the revolving body 70 to oppose the X-ray tube assembly 20, and detects X-ray projected from the X-ray tube assembly 20 onto the test body.

The heat radiator 40 is provided in the revolving body 70 near the X-ray tube assembly 20, and discharges heat generated by the X-ray tube assembly 20. Further, in the heat radiator 40, a heat storage material 50 is provided for accumulating the heat generated by the X-ray tube assembly 20. The X-ray CT scanner is configured so that the heat radiator 40 is to be faced to a fan unit 60 when the revolving body 70 is in a non-operated state. In place of the fan unit 60, a radiator may be employed. A fan-and-radiator configuration may be employed.

The fan unit 60 is provided outside the revolving body 70, and circulates the heat discharged from the heat radiator 40 into a gap 80 formed by the revolving body 70 and the gantry cover 10, inside the gantry 5. The heat circulated by the fan unit 60 is discharged to the outside of the gantry cover 10 by an air blower (not shown) provided outside the revolving body 70. In this embodiment, two fan units 60 are provided at the two sides of the X-ray tube assembly 20. However, the number of fan units is changeable depending on the magnitude of heat radiation. Together with the air blower or alternatively without the air blower, a radiator or the like may be provided so as to improve the cooling efficiency. Holes may be provided in the outer periphery of the gantry cover 10 so as to improve the cooling efficiency.

The revolving body 70 is of a torus shape, and has a revolving axis at the center. The parts inside the revolving body 70, such as the X-ray tube assembly 20, the X-ray detector 30 and the heat radiator 40, revolve around the test body while projecting the X-ray thereonto in order to acquire various cross-sectional information of the test body.

The operation of the embodiment will be described below.

In order to acquire information on the test body, X-ray is projected from the X-ray tube assembly 20 while the revolving body 70 is revolved. X-ray is projected from the X-ray tube assembly 20 onto the test body, and the X-ray detector 30 arranged opposite to the X-ray tube assembly 20 detects the X-ray projected onto and transmitted through the test body.

Figure 2:
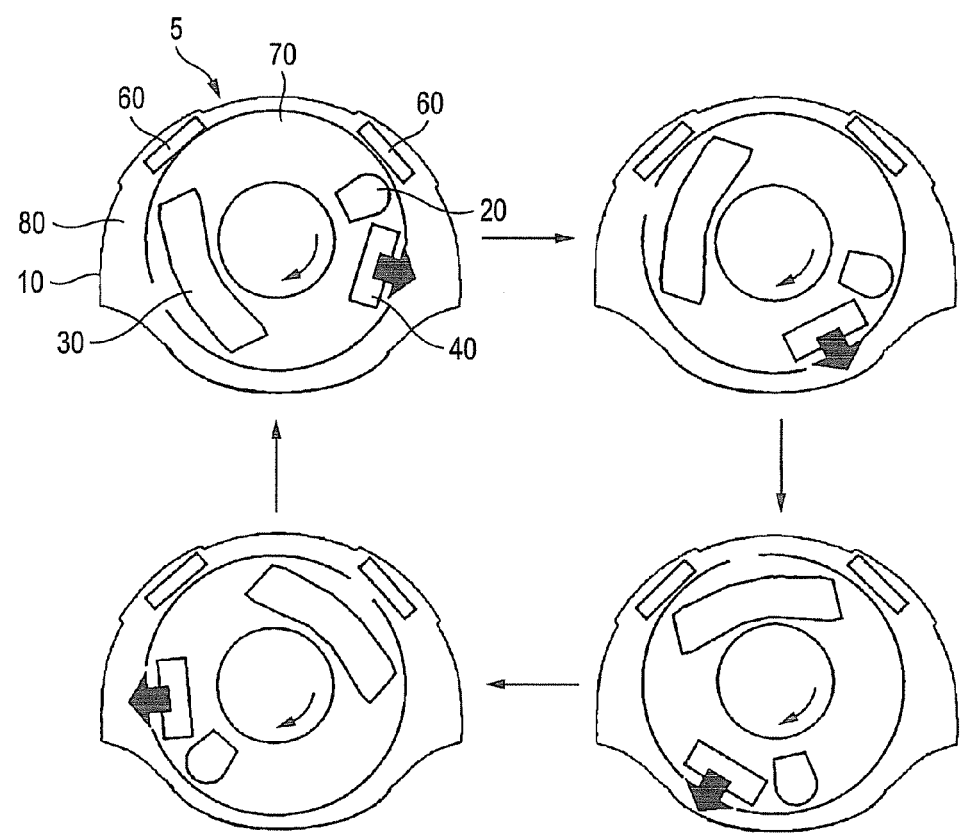
FIG. 2 illustrates an operation of the X-ray CT scanner according to the embodiment.

FIG. 2 illustrates four situations that the revolving body 70 is revolved for testing the test body. Here, the heat storage material 50 inside the heat radiator 40 is omitted in the figure for simplicity.

The heat is generated by the X-ray tube assembly 20 during X-ray projection and is radiated by the heat radiator 40 into the gap 80 between the revolving body 70 and the gantry cover 10. If the generated heat is discharged and scattered into the gap 80 during the revolution of the revolving body 70, a temperature inside the gantry 5 is risen.

Thus, in order to prevent the temperature rise inside the gantry 5 when the X-ray tube assembly 20 projects X-ray (when the revolving body 70 revolves), the heat storage material 50 is provided inside the heat radiator 40 so that the heat generated by the X-ray tube assembly 20 is accumulated. By providing the heat storage material 50, during the X-ray projection, the heat generated by the X-ray tube assembly 20 is prevented from circulating into the gap 80 between the revolving body 70 and the gantry cover 10.

Figure 3:
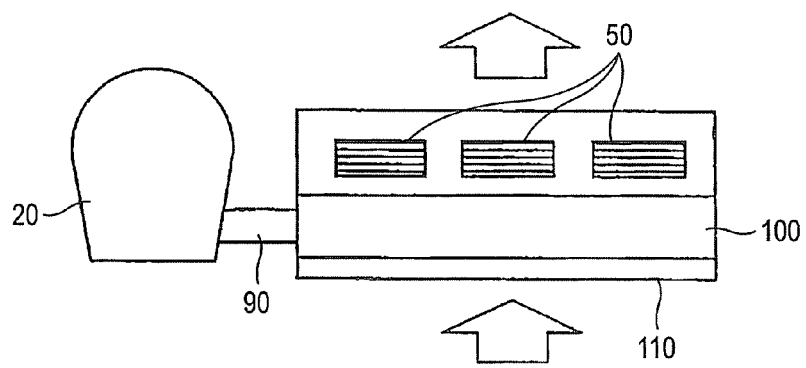
FIG. 3 illustrates a heat radiator.

FIG. 3 illustrates a detail of the heat radiator 40.

The heat radiator 40 of the present embodiment is connected to the X-ray tube assembly 20 through a pipe 90, and has: a heat storage material 50 for absorbing heat; a heat exchanging part 100 for absorbing the heat generated by the X-ray tube assembly 20 and cooling the X-ray tube assembly 20; and a heat sink 110 for improving the cooling effect.

According to the above configuration, the heat generated by the X-ray tube of the X-ray tube assembly 20 is supplied through the pipe 90 to the heat exchanging part 100, and then accumulated into the heat storage material 50 inside the heat radiator 40.

The heat exchanging part 100 accommodates, for example, the pipe 90 that is in a folded state and connected to the X-ray tube assembly 20. In the heat radiator 40, the pipe 90 circulates inside the heat exchanging part 100 such that the heat from the X-ray tube assembly 20 should be discharged and that the X-ray tube assembly 20 should be cooled. The heat sink 110 may be provided with a fan (not shown) so that air may be circulated in the direction of an arrow shown in FIG. 3. Here, the heat storage material 50 is removable, and hence may be exchanged appropriately depending on the situation of use of the X-ray CT scanner. For example, the heat storage material 50 is exchanged when the X-ray CT scanner is used for a long time and the heat absorption saturation of the heat storage material 50 is conceivable.

The X-ray CT scanner is controlled to be in a state shown in FIG. 1 when the revolving body 70 is in a non-operated state. Thus, the heat accumulated in the heat storage material 50 of the heat radiator 40 is circulated by the fan unit 60 into the gap 80 formed by the revolving body 70 and the gantry cover 10. The heat circulated inside the gantry 5 is cooled through the above-described process.

As described above, a temperature rise inside the revolving body 70 is avoided, and hence the inside of the gantry 5 can be cooled efficiently.

Figure 4:
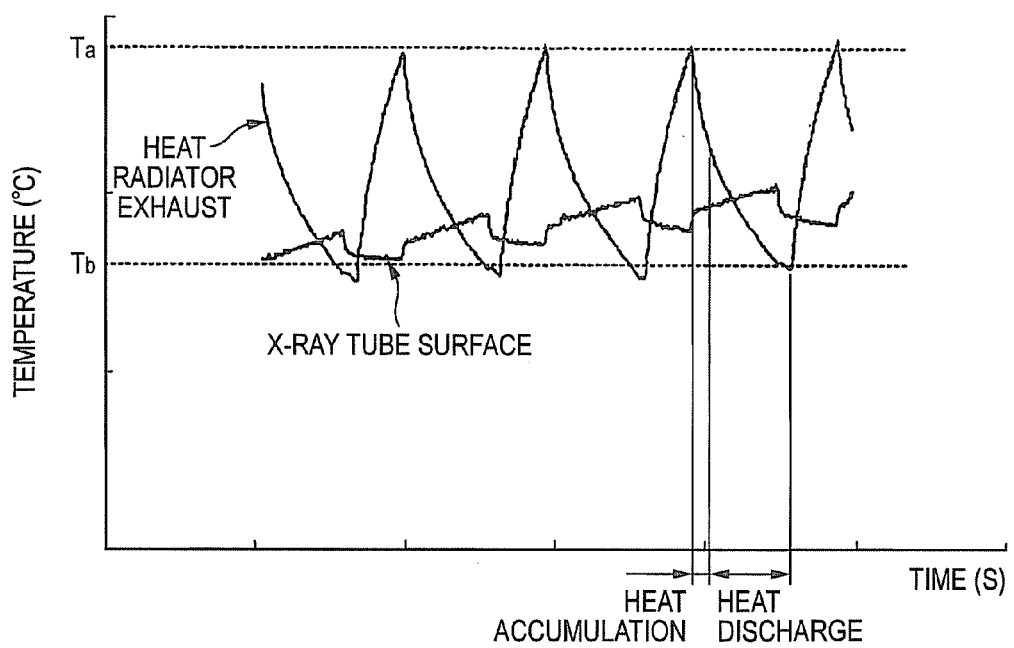
FIG. 4 illustrates a temperature change in a heat radiator and in an X-ray tube assembly during the use of an X-ray CT scanner.

FIG. 4 illustrates a temperature change in the heat radiator 40 and in the X-ray tube assembly 20 during the operation of the X-ray CT scanner. The horizontal axis indicates time (s), while the vertical axis indicates temperature (° C.). As shown in FIG. 4, during the X-ray projection by the X-ray tube assembly 20, heat is generated by the X-ray tube and hence the temperature rises. At that time, the heat generated by the X-ray tube is scattered through the revolution of the revolving body 70 so that a temperature rise is caused in the heat radiator 40.

In general, when the temperature inside the revolving body 70 reaches near 37° C., in the X-ray CT scanner, a noise or the like is generated in the acquired X-ray image so that acquisition of a clear X-ray image becomes difficult.

Thus, in this embodiment, the heat generated by the X-ray tube assembly 20 during X-ray projection is absorbed by the heat storage material 50 provided in the heat radiator 40 so that the discharge of the heat into the gap 80 is reduced. As a result, the temperature rise inside the gantry 5 is suppressed. As the heat storage material 50, an appropriate material is selected based on the temperature inside the revolving body 70 with taking into consideration the melting point and the melting heat of the heat storage material 50. FIG. 5 lists types of heat storage material 50 together with their melting point values and melting heat values.

For example, according to the following Formula (1), when X-ray projection is performed for 2 seconds at an output of 130 kV and 350 mA, 91 kJ of heat is generated.

$$E = V \cdot \int I \cdot dt \qquad \text{(Formula 1)}$$

where E denotes the Joule heat (J), I denotes the current (A), and V denotes the potential difference (V).

At that time, it is assumed that the temperature inside the revolving body 70 reaches 50° C. and that sodium thiosulfate hydrate having a melting point of 48° C. is employed. Then, the melting heat of sodium thiosulfate is 197 kJ/kg. Thus, in order to absorb the total heat generated in the X-ray tube during X-ray projection, approximately 460 g of sodium thiosulfate hydrate is necessary.

As described above, an appropriate heat storage material may be selected in accordance with the temperature change in the X-ray CT scanner.

According to the present embodiment, even when the heat generated by the X-ray tube and the like is accumulated inside the gantry 5, the inside of the gantry 5 can be cooled efficiently.

The present invention is not limited to the embodiment described above, and appropriate design change may be performed without departing from the spirit of the invention.

What is claimed is:

1. An X-ray CT scanner comprising:
   a gantry;
   a revolving body provided inside the gantry and capable of rotation;
   an X-ray tube assembly provided within the revolving body, proximate an outer surface thereof;
   an X-ray detector provided within inside the revolving body positioned proximate an outer surface thereof, opposite to the X-ray tube assembly;
   a heat radiator, provided within the revolving body, said heat radiator thermally coupled to the X-ray tube assembly by a heat transfer member, said heat radiator comprising:
      a heat storage material thermally coupled to the heat transfer member, wherein said heat storage material is one of a hydrated inorganic salt or an organic compound, said inorganic salt or organic compound having a melting heat of from 157 kJ/kg to 264 kJ/kg;
      a heat exchanger part thermally coupled to the heat storage material; and
      a heat sink thermally coupled to the heat exchanger, wherein said heat sink is provided proximate the outer surface of the revolving body;
   a fan provided on an inner surface of the gantry, said fan positioned to be aligned with said heat radiator when said revolving body is stationary.

2. The X-ray CT scanner of claim 1, wherein the heat storage material is removable from the heat radiator.

3. The X-ray CT scanner of claim 1, wherein the revolving body has a torus shape.

4. The X-ray CT scanner of claim 1, wherein the fan is configured to transfer heat from said heat storage material into a gap formed by the revolving body and the gantry.

5. An X-ray CT scanner comprising:
   a gantry;

a revolving body provided inside the gantry and capable of rotation;

an X-ray tube assembly provided inside the revolving body;

a heat radiator provided inside the revolving body, wherein the heat radiator comprises:
- a heat transfer member connected to the X-ray tube assembly to receive heat therefrom,
- a heat storage material connected to the heat transfer member and configured to store heat received from the X-ray tube assembly, wherein said heat storage material is selected from materials that melt at a temperature from 28.2° C. to 58° C., and
- a heat sink thermally coupled to the heat storage material;

an X-ray detector provided inside the revolving body positioned opposite to the X-ray tube assembly; and a cooling unit provided outside the revolving body, cooling unit including at least one of a fan and a radiator and positioned to be thermally coupled with the heat radiator when the revolving body is stationary.

6. The X-ray CT scanner of claim 5,
wherein the cooling unit is configured to cool the heat storage material and to discharge the received heat from the heat storage material to outside the revolving body.

7. The X-ray CT scanner of claim 6, wherein the cooling unit comprises a fan that is configured to transfer heat from said heat storage material into a gap formed by the revolving body and the gantry.

8. The X-ray CT scanner of claim 5,
wherein the heat storage material is removable from the heat radiator.

9. The X-ray CT scanner of claim 5, wherein the revolving body has a torus shape.

* * * * *